US00PP13067P2

(12) United States Plant Patent
Noodelijk

(10) Patent No.: US PP13,067 P2
(45) Date of Patent: Oct. 8, 2002

(54) CHRYSANTHEMUM PLANT NAMED 'AMOR CORAL'

(75) Inventor: Robert Noodelijk, Woubrugge (NL)

(73) Assignee: Chrysanthemum Breeders Association NV (NL)

( * ) Notice: Subject to any disclaimer, the term of this patent is extended or adjusted under 35 U.S.C. 154(b) by 0 days.

(21) Appl. No.: 09/734,605

(22) Filed: Dec. 13, 2000

(51) Int. Cl.[7] ..... A01H 5/00
(52) U.S. Cl. ..... Plt./291
(58) Field of Search ..... Plt./291

*Primary Examiner*—Bruce R. Campell
*Assistant Examiner*—Anne Marie Grünberg
(74) *Attorney, Agent, or Firm*—Parkhurst & Wendel, L.L.P.

(57) ABSTRACT

A chrysanthemum plant named 'AMOR CORAL' characterized by its medium sized blooms with coral ray florets and prolific branching; natural season flower date September 4–9; blooming for a period of 7 weeks.

3 Drawing Sheets

RELATED CULTIVARS

'AMOR CORAL' is related to 'AMOR' (U.S. Plant patent application Ser. No. 09/734,607) and 'AMOR WHITE'. Both 'AMOR CORAL' and 'AMOR WHITE' are color mutants of 'AMOR'.

BACKGROUND OF THE INVENTION

'AMOR CORAL' is a product of a breeding and selection program which had the objective of finding color mutants of 'AMOR'. The new plant of the present invention comprises a new and distinct cultivar of chrysanthemum plant that is a natural occurring sport of a parent chrysanthemum named 'AMOR'. A comparison with Parent chrysanthemum 'AMOR' is also made in this application. The new cultivar was discovered as a sport in September 1998 by Rob Noodelijk in a controlled environment (greenhouse) in Rijsenhout, Holland. The first act of asexual reproduction of 'AMOR CORAL' was accomplished when vegetative cuttings were taken from the initial selection in October 1998 in Rijsenhout, Holland. The new cultivar has been found to retain its distinctive characteristics through successive propagations.

BRIEF DESCRIPTION OF THE DRAWINGS

The present invention of a new and distinct variety of chrysanthemum is shown in the accompanying drawings, the color being as nearly true as possible with color photographs of this type.

DESCRIPTION OF THE INVENTION

Figure 1:
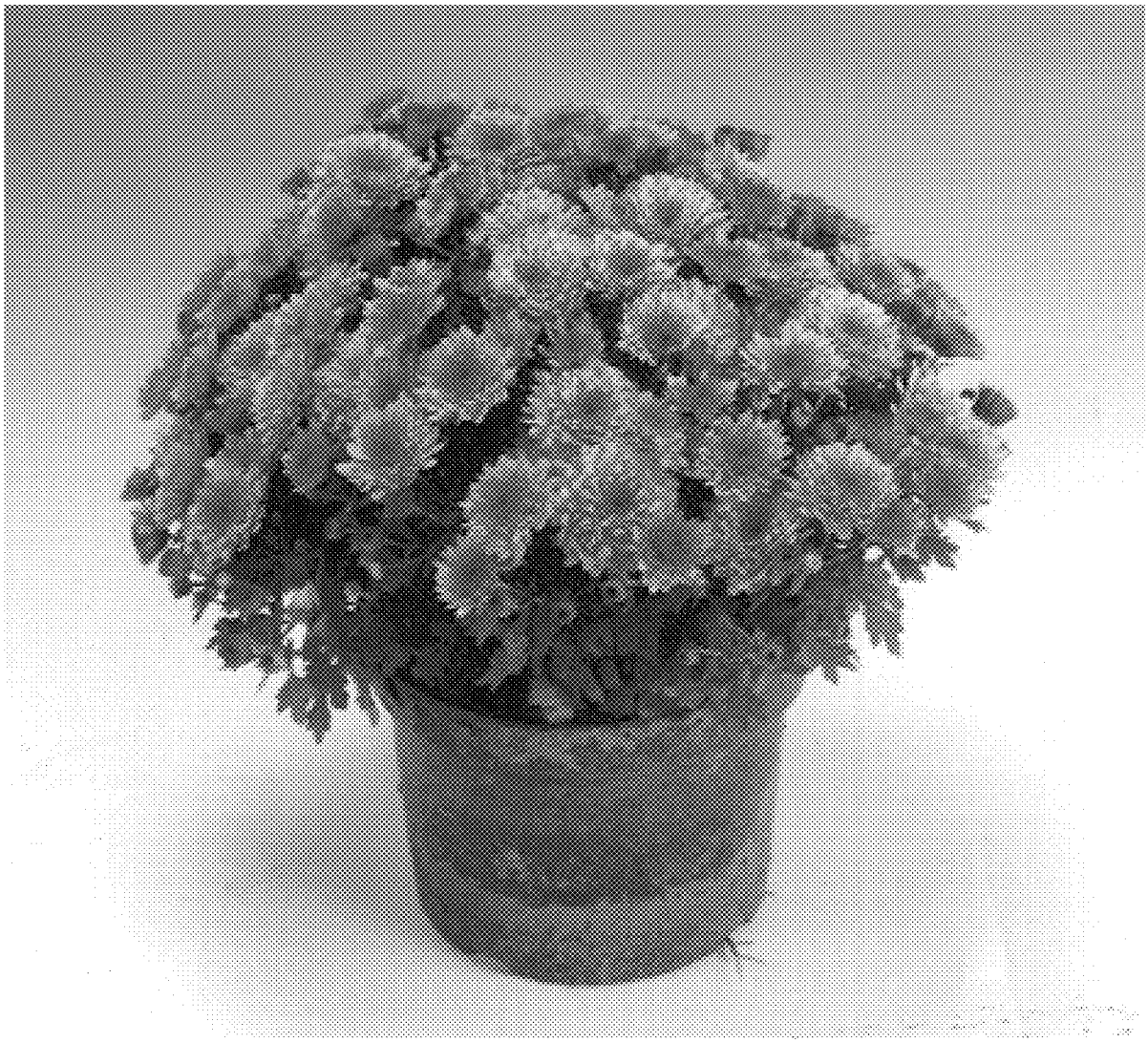
FIG. 1 shows a plant of the cultivar in full bloom.
Figure 2:
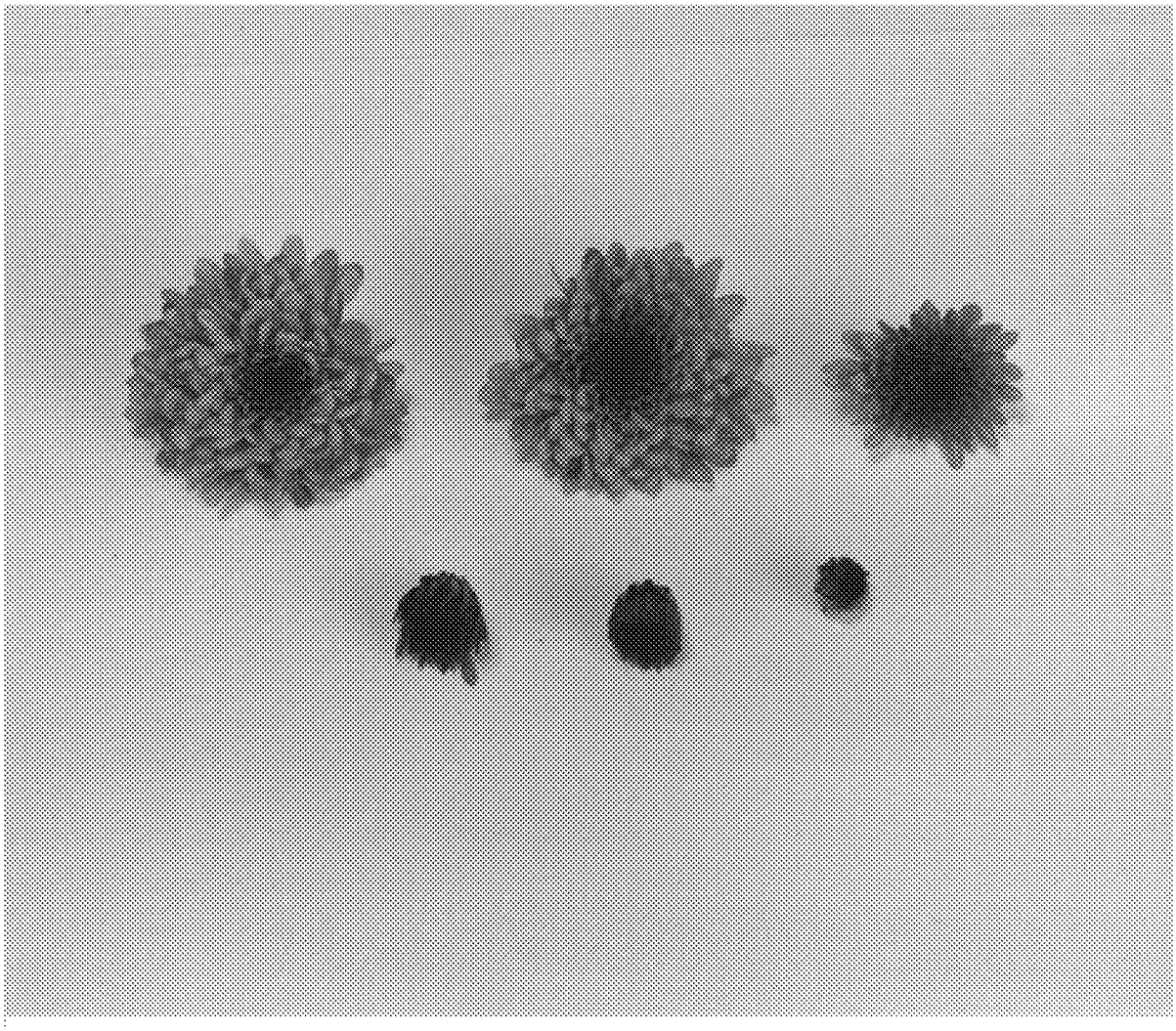
FIG. 2 shows the various stages of bloom of the new cultivar.
Figure 3:
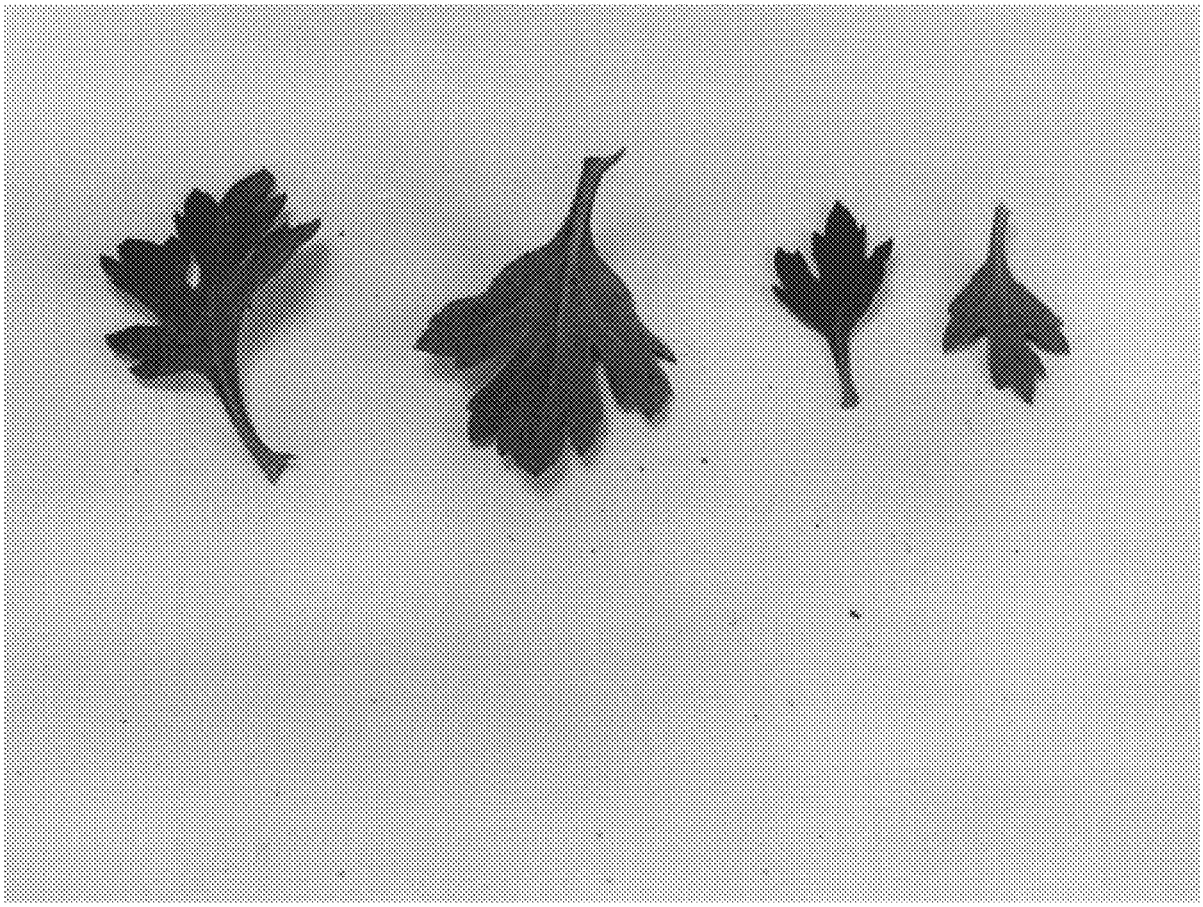
FIG. 3 shows the various stages of foliage and petiole of the new cultivar.

This new variety of chrysanthemum is of the botanical classification *Chrysanthemum morifolium*. The observations and measurements were gathered from plants grown out door in Rijsenhout, Holland under natural day length and temperature and planted week 22 in 1999 and 2000. The natural blooming date of this crop was September 4–9 (week 36). The average height of the plants was 30–35 CM cms. No growth retardants were used. No tests were done on disease or insects resistance or susceptibility. No tests were done on cold or drought resistance. This new variety produces medium sized blooms with coral ray florets and a dark coral center blooming for a period of 7 weeks.

From the cultivars known to inventor the most similar existing cultivar in comparison to 'AMOR CORAL' are 'AMOR' and 'AMOR WHITE'. When 'AMOR', 'AMOR WHITE' and 'AMOR CORAL' are being compared the following differences are noticed: The differences of 'AMOR', 'AMOR WHITE' and 'AMOR CORAL' are (1) Flower color and (2) Vigour. All other characteristics of 'AMOR' and 'AMOR CORAL' are similar.

(1) Flower color; 'AMOR CORAL' is a color mutant of 'AMOR' bearing coral blooms instead of pink blooms, 'AMOR WHITE' has white blooms instead of pink blooms.

(2) Vigour: The plants of 'AMOR CORAL' tend to be a little less vigorous than 'AMOR'. 'AMOR WHITE' is the opposite being a little more vigorous than 'AMOR'. These differences are small.

The following is a description of the plant and characteristics that distinguish 'AMOR CORAL' as a new and distinct variety.

The color designations are taken from the plant itself. Accordingly, any discrepancies between the color designations and the colors depicted in the photographs are due to photographic tolerances. The color chart used in this description is: The Royal Horticultural Society Colour Chart, edition 1995.

Table 1: Botanical Decription of Cultivar 'Amor Coral'

Bud:
- *Size*.—Medium; cross-section 1.2 cm, height 1.0 cm.
- *Outside color*.—Red-purple 60 D.
- *Involucral bracts*.—2 rows, length 7 mm, width 3 mm.
- *Involucral bracts among disc-florets*.—Not present.
- *Involucral bracts color*.—Green 138 B.

Bloom:
- *Type*.—Decorative.
- *Height*.—High, 3.0–3.5 cm.
- *Size*.—Medium.
- *Fully expanded*.—5.0–5.5 cm.
- *Number of blooms per branch*.—Approx. 5 blooms per branch.

*Performance on the plant*.—7 weeks.
*Seeds* (*if crossed*).—Produced in small quantities, ovate. Grey-brown 199 A, 1½ mm in length.
*Fragrance*.—Typical chrysanthemum.

Color:
*Center of the flower* (*disc-florets*).—Immature red-purple 60 D. Mature red-purple 60 D.
*Color of upper surface of the ray-florets*.—Red-purple 63 C.
*Color of the lower surface of the ray-florets*.—Red-purple 62 C.
*Tonality from distance*.—Mounded decorative garden mum with coral blooms.
*Color of the upper surface of the flowers after aging of the plant*.— To 62 C.

Ray florets:
*Texture*.—Upper and under side smooth.
*Number*.—200–230.
*Cross-section*.—Concave.
*Longitudinal axis of majority*.—Incurved to straight.
*Length of corolla tube*.—Medium, 0.9–1.1 cm.
*Ray-floret margin*.—Entire.
*Ray-floret length*.—2.5–2.8 cm.
*Ray-floret width*.—0.4–0.6 cm.
*Ratio length/width*.—High.
*Shape of tip*.—Pointed.
*Disc florets*.—Not present.

Reproductive organs:
*Stamen*.—Not present.
*Pollen*.—Not present.
*Styles*.—Thin.
*Style color*.—Yellow-green 144 A.
*Style length*.—4 mm.
*Stigmas color*.—Yellow-green 144 A.
*Stigma width*.—1 mm.
*Ovaries*.—Enclosed in calyx.
*Plant*.—Grown as a spray-type-pot-mum, outdoor.
*Shape*.—Mounded and round.
*Growth habit*.—Spreading.
*Growth rate*.—Moderate.
*Height*.—30–35 cm.
*Width*.—35–40 cm.
*Stem color*.—Green 138 B.
*Stem strength*.—Strong.
*Stem brittleness*.—Present.
*Stem anthocyanin coloration*.—Present, a thin layer of greyed-red 181 A mainly at the base of the stem.
*Length of lateral branch*.—From top to bottom 11–12 cm.
*Lateral branch color*.—Green 138 B.
*Lateral branch, attachment*.—Weak.
*Branching* (*average number of lateral branches*).—Mounding and prolific with 8–10 breaks after pinching.
*Peduncle length*.—3.5–4.5 cm.
*Peduncle color*.—Green 138 B.
*Natural season blooming date*.—September 4–9.

Foliage:
*Color of mature leaves*.—Upper side green 138 A. Under side green 138 B.
*Color of immature leaves*.—Upper side green 138 A. Under side green 138 B.
*Size*.—Small; length 6 cm, width 5 cm.
*Quantity* (*number per lateral branch*).—12–14.
*Shape*.—Oval.
*Texture upper side*.—Glabrous.
*Texture under side*.—Pubescent.
*Venation arrangement*.—Palmate.
*Shape of the margin*.—Serrated.
*Shape of base of sinus between lateral lobes*.—Acute.
*Margin of sinus between lateral lobes*.—Diverging.
*Shape of base*.—Asymmetric.
*Apex*.—Mucronate.

TABLE 2

| | Differences with the comparision varieties (when grown under the same conditions) | | |
|---|---|---|---|
| | 'AMOR CORAL ' | 'AMOR WHITE' | 'AMOR' |
| Color of the celter of the flower | Immature red-purple 60 D Mature red-purple 60 D | Immature white 155 A Mature white 155 B | Immature red-purple 74 B Mature red-purple 74 D |
| Color of the upper surface | Red-purple 63 C | White 155 D | Red-purple 74 C |
| Color of the lower surface | Red-purple 62 C | White 155 D | Red-purple 74 D |
| Length of lateral branch | 12–13 cm | 14–15 cm | 12–13 cm |
| Plant Height | 30–35 cm | 32–38 cm | 32–36 cm |

I claim:

1. A new and distinct variety of chrysanthemum plant as described and illustrated.

* * * * *